United States Patent [19]

Takeuchi

[11] 4,366,119
[45] Dec. 28, 1982

[54] DISCRETE TYPE AUTOMATED CHEMICAL ANALYTIC APPARATUS

[75] Inventor: Masaki Takeuchi, Otawara, Japan

[73] Assignee: Tokyo Shibaura Denki Kabushiki Kaisha, Japan

[21] Appl. No.: 243,737

[22] Filed: Mar. 16, 1981

[30] Foreign Application Priority Data

Mar. 20, 1980 [JP] Japan .................................. 55-34953

[51] Int. Cl.³ ..................... G01N 33/48; G01N 35/06; G01N 35/04
[52] U.S. Cl. .................................... 422/65; 364/497; 422/67; 422/100
[58] Field of Search ....................... 422/64, 65, 66, 67, 422/100, 103; 141/130; 364/497, 498

[56] References Cited

U.S. PATENT DOCUMENTS

| | | | |
|---|---|---|---|
| 3,481,709 | 12/1969 | Slone | 422/66 |
| 3,551,112 | 12/1970 | Sequeira et al. | 422/65 |
| 3,576,605 | 4/1971 | Drake et al. | 422/65 X |
| 3,687,632 | 8/1972 | Natelson | 422/65 X |
| 3,723,066 | 3/1973 | Moran | 422/66 X |
| 4,260,581 | 4/1981 | Sakurada | 422/65 |
| 4,265,855 | 5/1981 | Mandle et al. | 422/65 |
| 4,299,796 | 11/1981 | Hogen Esch | 422/65 X |

Primary Examiner—Michael S. Marcus
Attorney, Agent, or Firm—Finnegan, Henderson, Farabow, Garrett & Dunner

[57] ABSTRACT

A discrete type automated chemical analytic apparatus, wherein a carrier is made movable through a path defined above a reaction line in order to pipette a specimen and reagent into the selected one of a plurality of reaction tubes linearly mounted on the top run of an endless belt. A specimen container and reagent containers are set side by side above the extension of the reaction line. Nozzles are mounted on the carrier in a vertically movable state to draw out the contents of the specimen container and reagent containers. The carrier is moved to any selected point on the reaction line by a motor with the aid of a belt conveyor connected to said carrier, and a pair of pulleys across which the belt conveyor is stretched.

15 Claims, 9 Drawing Figures

F I G. 7
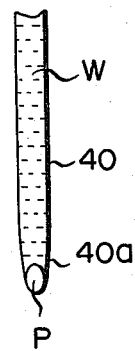
F I G. 9
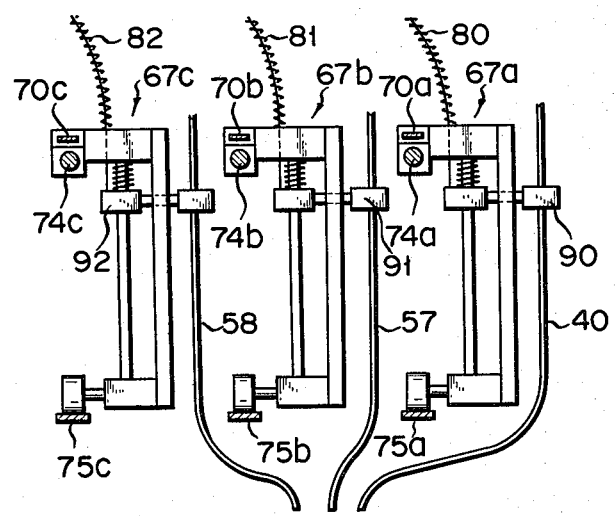

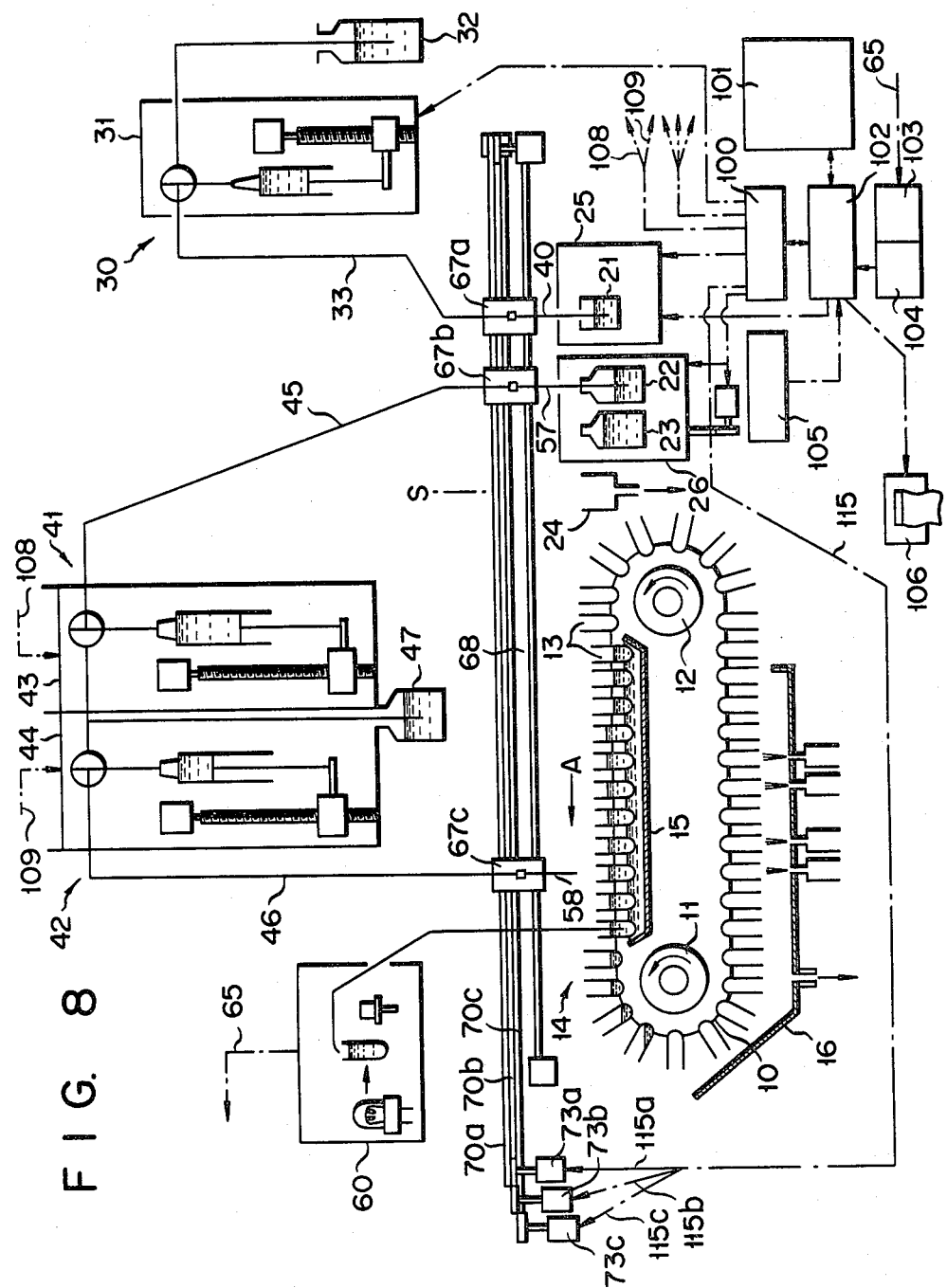

DISCRETE TYPE AUTOMATED CHEMICAL ANALYTIC APPARATUS

This invention relates to an automated analytic apparatus, and more particularly to the so-called discrete type automated chemical analytic apparatus which is capable of continuously analyzing a large number of specimens with respect to a plurality of items of examination in a single reaction channel.

Recently, it has assumed greater importance to carry out the analytic procedure of a specimen for diagnosis of a disease and provide required data. Moreover, the number of specimens and their item of examination are progressively increasing. In view of such circumstances, therefore, automation of an analytic procedure has become a problem of urgency in hospitals, laboratories or centers which undertake medical examination work. What is most demanded in this case is an improved automated chemical analytic apparatus which enables a limited personnel and space to furnish analytic diagnostic data closely related to human life without errors.

In this connection, the following points should be taken into consideration:

(1) Analysis of an extremely minute amount of a specimen and reagent should be carried out at low cost.

(2) A large number of specimens should be quickly analyzed and the resultant data should be immediately obtained.

(3) A limited personnel should be enabled to carry out analytic procedures of a larger number of specimens with respect to numerous items of examination.

(4) Accurate and precise data should be furnished in good time.

(5) The subject analytic apparatus should be made sufficiently compact to be installed in a limited space.

With the conventional automated analytic apparatus, noticeable improvements have been made in respect of the above-listed requirements. Particularly with the first and second items, noteworthy improvements have been accomplished. With the other items, however, improvements attempted to-date can not be regarded as fully satisfactory.

The known discrete type automated chemical analytic apparatus in general use is of the so-called fixed type, wherein the points at which a specimen and reagent are pipetted are fixed, in other words, a distance between a pipetting pump and pipetting point is always defined in accordance with an item of examination. Some semifixed type analytic apparatuses have also been proposed wherein the pipetting point can be slightly shifted, if necessary. Generally speaking, has been developed wherein the pipetting point can not be freely varied in a conventional analytic apparatus. In other words, the prior art analytic apparatus is not of the type which enables a given amount of a reagent or specimen to be pipetted at any desired point along a reaction line. Therefore, limitation is imposed on the conventional analytic apparatus in respect of the latitude of application, that is, in the sense that a reaction time should be properly chosen in accordance with individual reagents and specimens. Inevitably, therefore, occasions arise in which an improper reaction has to be undertaken, resulting in a decline in the reliability of obtained data of examination.

Consequently, the examiner has hitherto manually changed a pipetting point or an amount of a liquid to be pipetted in order to obtain more accurate data. Demand has therefore been made to automate these manual procedures.

For reference, the aforementioned analytic apparatus is disclosed in the U.S. Pat. No. 3,432,271. In this connection, the Japanese patent disclosure No. 54-5790 may be cited which has attempted to automate the pipetting of a reagent in order to simplify the control of an automated chemical analytic apparatus. Brief description is now given with reference to FIG. 1 of the arrangement of the chemical analytic apparatus of said Japanese patent disclosure No. 54-5790. This disclosed analytic apparatus comprises:

(a) a serum pipetting mechanism periodically repeating the same action regardless of specimen data;

(b) a nozzle through which a serum sample is supplied as a specimen from the mechanism (a);

(c) a washing tank used to clean the outer wall of the nozzle (b);

(d) a main computer for sending forth an instruction based on specimen data;

(e) a large number of first reagent containers;

(f) a turntable on which the first reagent containers (e) are carried and which is driven upon receipt of an instruction from the main computer (d);

(g) a pipette mechanism for dripping the first reagent;

(h) a nozzle connected to said pipette mechanism (g);

(i) a washing tank used to clean the outer wall of the nozzle (h);

(j) a large number of second reagent containers;

(k) a turntable on which the second reagent containers (j) are carried and which is driven upon receipt of an instruction from the main computer (d);

(l) a pipette mechanism for dripping the second reagent;

(m) a nozzle connected to the pipette mechanism (l); and (n) a washing tank used to clean the outer wall of the nozzle (m).

Description is now given of the operation of an automated chemical analytic apparatus (FIG. 1) set forth in the Japanese patent disclosure 54-5790. This chemical analytic apparatus further comprises a specimen feeder (q) carrying a plurality of linearly arranged specimen container (p) each holding, for example, serum. Where one of the specimen containers (p) is brought to a point at which a serum is sucked out of the container (p), then the specimen feeder (q) temporarily ceases to be moved. During the rest of the specimen feeder (q), the aforesaid pipette mechanisms (a, g, l) carry out a prescribed action on a reaction line (s) along which a large number of reaction tubes (r) are set side by side. The serum sucked out of the serum container (p) by the pipette mechanism (a) is diluted with demineralized water. The diluted serum is pipetted from the specimen container (p) into the corresponding one of the reaction tubes (r) linearly arranged on the reaction line (s) through the nozzle (b). Where one of the reaction tubes (r) is made to face the nozzle (h) for the first reagent while traveling to the right as viewed in FIG. 1, then the turntable (f) for the first reagent is rotated in the direction of an indicated arrow to an extent corresponding to the previously supplied specimen data. When the rotation is brought to rest, the first reagent held in the reagent container (e) set as a prescribed pipetting point is dripped into the reaction tube (r) by the pipette mechanism (g). Where the reaction tube (r) further travels to the second reagent nozzle (m), then the second reagent is drawn into the reaction tube (r) by the pipette mechanism (l).

The serum solution which was subjected to the above-mentioned reaction procedure has its composition is determined by a spectroscope (t) disposed at the terminal end of the reaction line. The result of the spectroscopic determination is transmitted to the main computer (d) through an interface device (u), and also is visibility printed out at an operation and control section (v).

Application of a turntable in the above-described chemical analytic apparatus of the Japanese patent disclosure No. 54-5790 enables a proper reagent to be automatically selected, eliminating the troublesome work of manually exchanging reagent containers. Further, the analytic apparatus automates the suction and pipetting of a serum and reagent, and enables the uniform operation of a control system and the simplification of its arrangement, thereby assuring a high reliability.

With the aforementioned analytic apparatus, however, the points at which the suction and pipetting of a serum and reagent are carried out are all fixed in place. With the apparatus, therefore, it is impossible to control an interval between the point of time at which pipetting is carried out and that at which a final analysis is performed. For instance, even where a specimen requiring an instant analysis is presented and a reagent reaction relative to the specimen can be finished in a short time, the quick operation of the analytic apparatus of the above-mentioned disclosed patent application is obstructed by the rather lengthy reaction time prescribed in the specification, presenting difficulties in meeting urgent requirements. In other words, the apparatus lacks the freedom to match a reaction time with a specimen to be examined. This means that not only time loss but also an excessively protracted reaction between a serum and reagent results, leading to the production of inaccurate data. Moreover, with the analytic apparatus, turntables occupy a considerably large space, presenting difficulties in rendering the apparatus compact.

It is accordingly the object of this invention to provide a new discrete type automated chemical analytic apparatus which resolves drawbacks accompanying the previously described conventional automated chemical analytic apparatus, is capable of properly controlling a time of reaction between a specimen and reagent in accordance with the kind of the specimen and items of analysis, has a wider latitude of application than has been possible in the past, assures the quick examination of a large number of specimens, and is further rendered considerably compact.

The discrete type automated chemical analytic apparatus of this invention which has attained the above-described objects offers the following advantages.

(1) The points at which a specimen and reagent are pipetted can be selected quite freely, eliminating the occurrence of a waiting time which might otherwise occur before a specimen and reagent are pipetted into a reaction tube. In other words, the point of pipetting can be properly defined always to assure a minimum reaction time. Therefore, the present analytic apparatus meets the urgent examination of a specimen and conversely allows a reaction between a specimen and reagent to take a rather lengthy time.

Where a reaction rate assay is carried out in a cycle time of 30 seconds, with respect to, for example, lactic dehydrogenase, analysis of ten specimens can be conducted in a total time of 5 minutes 50 seconds, with 10 seconds allotted to the presetting of the conditions of said assay, 30 seconds allowed for waiting time, 5 minutes allotted to the assay, and 10 seconds allotted to the removal of the specimens and reagents. In other words, the ten specimens can be analyzed accurately and easily.

(2) The specimen and first and second reagents can be pipetted in any order, at any point and in any amount. Namely, the present analytic apparatus has a sufficiently wide latitude of application to meet numerous items and conditions of analysis, making it possible to specify optimum conditions of analysis and assure a high precision of analysis.

(3) It is unnecessary for an examiner to manually set the position of a reagent-pipetting nozzle. Namely, the position of the nozzle can be automatically defined by a program. A large number of reaction tubes arranged on a reaction line need not be provided with the corresponding reagent nozzles. Therefore, the arrangement of the reaction tubes can be simplified, and the work efficiency of the examiner is prominently elevated.

(4) With the conventional chemical analytic apparatus, a troublesome work of cleaning the interior of a syringe was involved, each time the items of examination were changed. However, the present invention eliminates such necessity. Namely, any other required reagent has only to be set at a prescribed spot. Consequently, the change of the items of examination and preparatory work for analysis can be finished in such a short time as can be counted in the unit of seconds, as against several minutes consumed in the prior art analytic apparatus.

(5) The reagent does not flow, as in the prior art, from the reagent suction nozzle to the syringe and then to the reagent discharge nozzle. With the present invention, a single nozzle is concurrently used for suction and discharge, preventing the reagent from entering the syringe, and consequently making it unnecessary to clean the interior of the syringe itself. It is possible to avoid the uneconomical practice of wasting a large amount of expensive reagents, each time they are exchanged.

BRIEF DESCRIPTION OF THE DRAWINGS

This invention can be more fully understood from the following detailed description when taken in conjunction with the accompanying drawings, in which:

FIG. 7 is an enlarged view of the end portion of the nozzle used with the apparatus of FIG. 2;

FIG. 8 schematically sets forth a discrete type automated chemical analytic apparatus according to a second embodiment of this invention; and FIG. 9 is an enlarged view of three separate carrier members included in the analytic apparatus of FIG. 8, as taken in the same direction as in FIG. 6.

Description is now given with reference to FIGS. 2 to 7 a discrete type automated chemical analytic apparatus according to a first embodiment of this invention.

Figure 1:
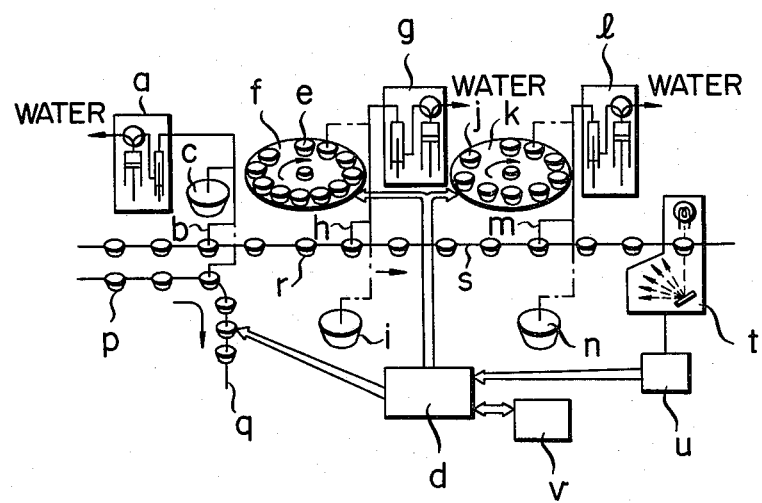
FIG. 1 schematically shows the arrangement of a prior art automated chemical analytic apparatus.
Figure 2:
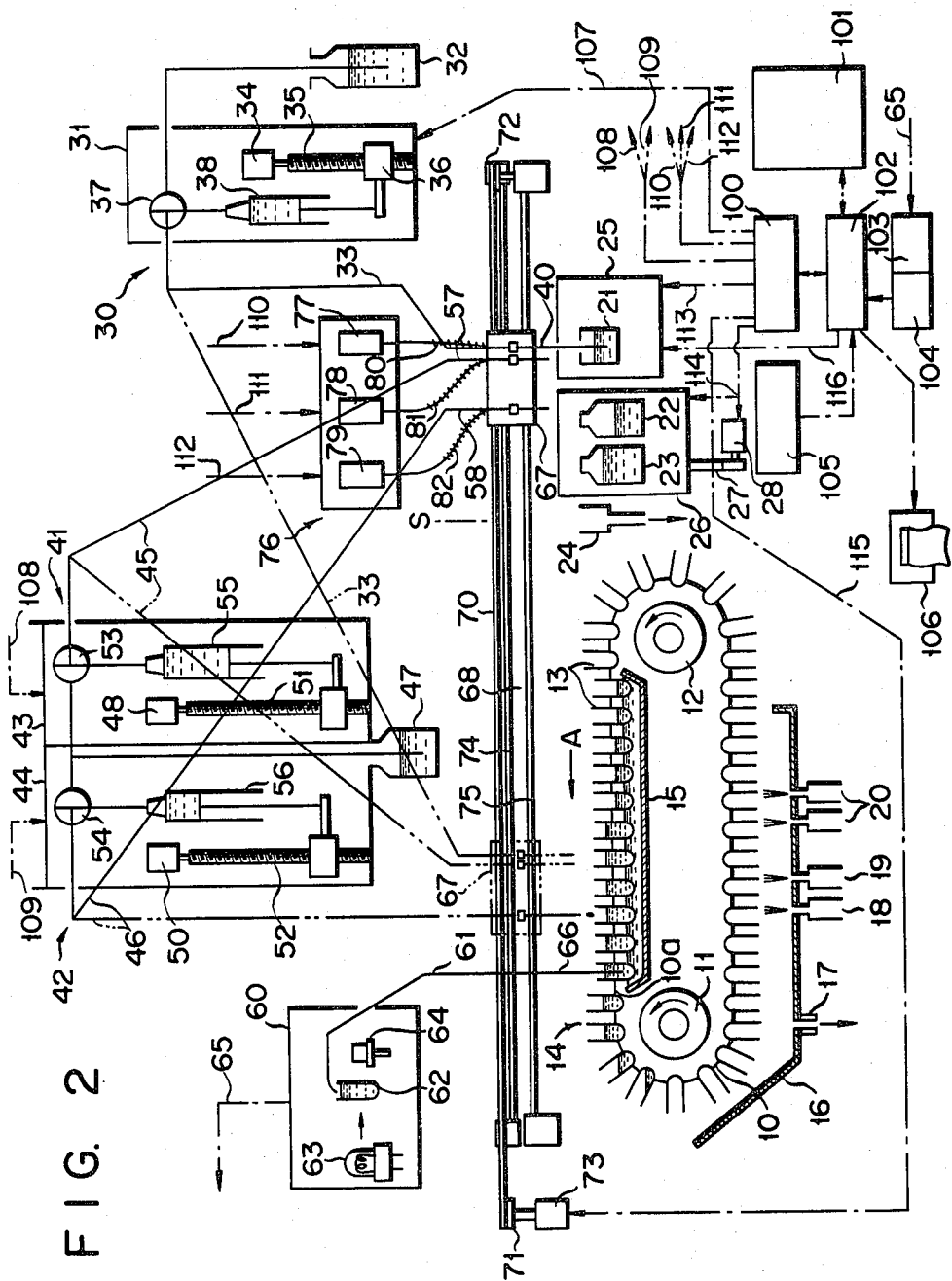
FIG. 2 schematically sets forth the arrangement of a discrete type automated chemical analytic apparatus according to a first embodiment of this invention.

Referring to FIG. 2, an endless conveyor belt 10 is driven by a pair of drive shafts 11, 12 rotated in the same direction indicated by the arrows. The top runs 10a of the conveyor belt 10 is intermittently moved in the direction of an arrow A. The total length of the conveyor belt 10 is fitted with a large number of reaction tubes 13 spatially arranged in the direction in which the conveyor belt 10 runs. A group of reaction tubes 13 positioned on the top run 10a defines a sustantially horizontal reaction line 14 for one channel (representing a single reaction line as used in the particular industry). The reaction tubes 13 set on the reaction line 14 are carried while being immersed in a thermostat bath 15. A downward inclined waste receptacle 16 is provided at the rear end of the conveyor belt 10. The receptacle 16 is fitted with an exhaust port 17, running water-ejecting nozzle 18, demineralized water-ejecting nozzle 19 and dry air-jetting nozzles 20 in the order mentioned as counted from the rear end of the conveyor belt 10. When brought to the bottom run side of the conveyor belt 10 these members are used to wash and dry the reaction tubes in order to render them ready for the subsequent application. A specimen container 21, first and second reagent containers 22, 23 and second water receptacle 24 are provided on the right side of the conveyor belt 10 as viewed in FIG. 2 in the order mentioned as counted from the right side. The specimen container 21 is held in a specimen cassette 25. The paired reagent containers 22, 23 are set in a reagent cassette 26. The reagent cassette 26 is connected to a drive pulse motor 28 by means of a belt pulley mechanism 27. The reagent cassette 26 is intermittently moved horizontally, that is, in a direction perpendicular to the surface of FIG. 2. Laterally arranged in the cassette 26 are containers of different reagents (not shown) in the paired form like the first and second reagent containers 22, 23. The horizontal movement of the cassette 26 causes any pair of reagent containers to be brought to a desired suction point.

With the foregoing embodiment, serum sampled from an examinee is used as a specimen. However, urine may be chosen as a specimen.

A specimen discharge mechanism 30 for pipetting a specimen from the specimen container 21 into any reaction tube 13 mounted on the reaction line 14 is positioned above the reaction line 14 or an extension thereof. The specimen discharge mechanism 30 comprises a specimen-feeding pump assembly 31, demineralized water bottle 32 connected to the specimen-feeding pump assembly 31 through a communication pipe to supply deionized water to the specimen-feeding pump assembly 31 and a flexible pipe 33 also connected to the specimen-feeding pump assembly 31. This specimen-feeding pump assembly 31 comprises a pulse motor 34, lead screw 35 driven by the pulse motor 34, nut member 36 threadedly engaged with the lead screw 35 and syringe 38 whose output terminal is connected to the flexible pipe 33 and deionized water bottle 32 through an electromagnetic switching valve 37, and whose input side piston rod is connected to a nut member 36. The free end portion of the flexible pipe 33 constitutes a nozzle 40 for the suction and pipetting of a specimen. The syringe 38 and flexible pipe 33 are always almost fully filled with deionized water.

Provided above the reaction line 14 are first and second reagent discharge mechanisms 41, 42 for pipetting first and second reagents from the corresponding containers 22, 23 into the selected one of the reaction tubes 13 mounted on the reaction line 14. The reagent discharge mechanisms 41, 42 have substantially the same arrangement as the specimen discharge mechanism 30. The reagent discharge mechanisms 41, 42 respectively comprise pump assemblies 43, 44, flexible pipes 45, 46 connected thereto, and a common deionized water bottle 47 connected to the pumps 43, 44 through pipes. The pump assemblies 43, 44 respectively comprise drive pulse motors 48, 50, nut members 51, 52 threadedly engaged therewith and syringes 55, 56 whose output terminals are connected to flexible pipes 45, 46 through 2-way electromagnetic switching valves 53, 54 and whose input terminal piston rods are connected to the corresponding nut members.

The free end portions of the flexible pipes 45, 46 constitute nozzles 57, 58. As in the specimen-feeding pump assembly 31, the syringes 55, 56 and flexible pipes 45, 46 of the first and second reagent discharge pumps 43, 44 are always almost fully filled with deionized water.

A spectroscopic unit 60 of the known type is provided above the terminal end portion of the reaction line 14. A reacted solution drawn out of the reaction tube 13 through a suction pipe 61 is brought into a flow cell 62. A light source 63 and detector 64 cooperate to make a spectroscopic measurement of the reacted solution taken into the flow cell 62. A signal indicative of the result of measuring the light absorptivity of the reacted solution is transmitted to a signal line 65. The suction pipe 61 is fitted with a known suction pump (not shown). The lower end portion of the suction pipe 61 acts as a suction nozzle 66. The suction nozzle 66 made to face the terminal end of the reaction line 14 is brought down, when required, to suck up a reacted solution from the reaction tube 13 brought to the terminal end of the reaction line 14. FIG. 2 shows the suction nozzle 66 brought down to a sucking state. The vertical movement of the suction nozzle 66 is effected by proper means, for example, a solenoid.

The specimen nozzle 40, and first and second reagent nozzles 57, 58 are vertically and spatially supported by a carrier member 67. This carrier member 67 is made movable along a horizontal path 68 positioned above the reaction line 14 and extension thereof in substantially parallel relationship therewith. The three nozzles 40, 57, 58 also move with the carrier member 67.

The reciprocation of the carrier member 67 through the path 68 is effected by the cooperation of a timing belt or string 70 fixed to the carrier member 67, a pair of right and left pulleys 72, 71 for stretching the belt 70 along the path 68 and drive pulse motor 73 connected to the left pulley 71.

Upper and lower parallel elongated guide bars 74, 75 horizontally extend along the path 68 to guide the carrier member 67 exactly along the path 68. The right and left ends of both bars 74, 75 are securely supported by proper means.

The three nozzles 40, 57, 58 supported by the carrier member 67 are normally set in a most retracted, namely, most lifted position, and, when required, are let to move vertically from the position into the corresponding specimen container 21 and first and second reagent containers 22, 23 to suck up the contents thereof. The vertical movement of the three nozzles 40, 57, 58 is effected by a solenoid mechanism 76 schematically set forth in FIG. 2.

Three solenoids 77, 78, 79 of the solenoid mechanism 76 are respectively connected to the corresponding nozzles 40, 57, 58 by means of flexible drive wires 80, 81, 82. The solenoids 77, 78, 79 are so arranged as to be retracted when energized and brought down when deenergized.

Figure 5:
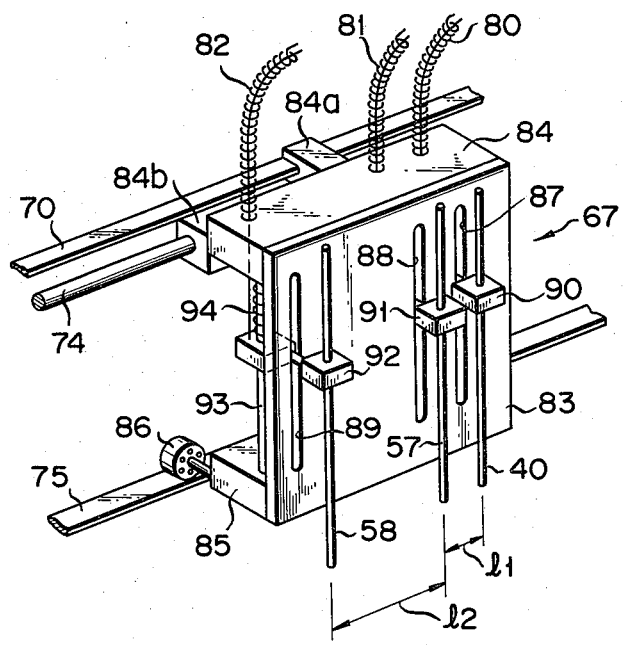
FIG. 5 is an enlarged oblique view of a carrier member indicated in FIG. 2.
Figure 6:
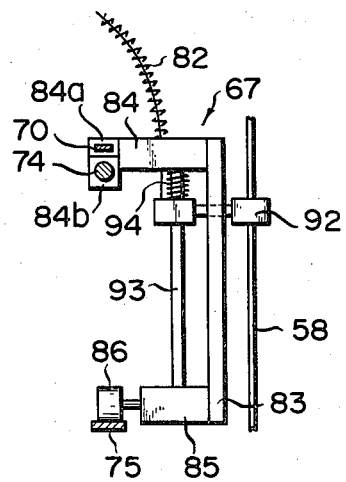
FIG. 6 is a side elevation of FIG. 5.

Description is now given with reference to FIGS. 5 and 6 of the carrier member 67 and associated members. The carrier member 67 comprises a vertical wall plate 83, upper laterally projecting block 84 fixed to the front or back side of the upper portion of the vertical wall plate 83 and lower block 85 fixed to the front or back side of the lower portion of said vertical wall plate 83 in a state laterally projecting in parallel with the upper block 84. A fixing block 84a and guide block 84b are rigidly fixed to the free edge portion of the upper block 84. An upper guide bar 74 having a round cross section is made to slide through the guide block 84b. The free edge portion of the lower block 85 is fitted with a guide roller 86. This guide roller 86 is made to roll over the surface of a flat lower guide bar 75. A pair of guide rollers 86 are actually provided, though not shown in FIGS. 5 and 6.

Three vertically elongated guide slots 87, 88, 89 are spatially formed in the vertical wall plate 83. The respective slots 87, 88, 89 are fitted with support elements 90, 91, 92 (one (92) of which is shown in FIG. 6). Each of these support elements 90, 91, 92 is enlarged into a block form at both ends, and made movable only vertically. Those of the block portions of the support elements 90, 91, 92 which project outward from the front side of the vertical wall plate 83 (as best shown in FIG. 6) are respectively penetrated by the specimen nozzle 40, first reagent nozzle 57 and second reagent nozzle 58. In FIGS. 5 and 6 the upper portions of these nozzles 40, 57, 58 are omitted.

A distance $l_1$ between the specimen nozzle 40 and first reagent nozzle 57 is specifically chosen to be smaller than the diameter of the opening of the reaction tube 13. A distance $l_2$ between the first and second reagent nozzles 57, 58 is particularly chosen to be substantially equal to a distance between the centers of the first and second reagent containers 22, 23.

As best shown in FIG. 6, the upper and lower blocks 84, 85 are bridged by three vertical guide rods 93, which respectively correspond to the vertical guide slots 87, 88, 89. Those of the block portions of the support elements 90, 91, 92 penetrating the vertical guide slots 87, 88, 89 which are positioned on the backside of the vertical wall plate 83 are made to slide along the corresponding guide rods 93. A compression spring 94 surrounds that section of the guide rod 93 of each of the support elements 90, 91, 92 which is defined between the underside of the upper block 84 and the upper surface of the inner block portion of each support element. The compression spring 94 always urges downward the support elements 90, 91, 92 or nozzles 40, 57, 58. However, the nozzles 40, 57, 58 can be electromagnetically retracted or lifted by means of drive wires 80, 81, 82 against the urging force of the compression spring 94. Where any of the solenoids 77, 78, 79 is deenergized, then the corresponding one of the nozzles 40, 57, 58 is brought down by the urging force of the compression spring 94.

The fact that the nozzle is normally electromagnetically retracted or lifted and, where necessary, is elastically brought down by the action of the compression spring 94 offers the advantage that should the lower end of the elastically movable nozzle be pressed against any obstruction, then the end is brought to rest there and prevented from being further let to move and consequently can be saved from damage or breakage.

The flexible pipes 33, 45, 46 connectable to the nozzles 40, 57, 58 within the range in which the carrier member 67 travels and the drive wires 80, 81, 82 corresponding the nozzles 40, 57, 58 should actually be made sufficiently long to facilitate the movement of the carrier member 67. In FIG. 2, however, the flexible pipe and wires are schematically illustrated regardless of the above-mentioned requirement.

Referring to the relationship between FIGS. 2 and 5, the pulleys 71, 72 of the timing belt 70 are shown in a state rotated through an angle of 90° in order to better show the pulse motor 73. However, it is to be understood that the pulleys 71, 72 and pulse motor 73 are rotated along a plane parallel with the surface of FIG. 2.

Description is now given with reference to FIG. 2 of an assembly of electronic circuit blocks 100 to 106 for automatically controlling the operations of the respective constituent mechanisms of a discrete type automated chemical analytic apparatus embodying this invention. The assembly comprises a control circuit 100 for sending forth various control signals; an operation panel 101; an interface device 102 connected between the operation panel 101 and control circuit 100; a log converter 103 for converting signals sent forth from the spectroscopic unit 60 which denote the results of analyzing a specimen into signals instructing further processing; an A-D converter 104 for converting an output signal from the log converter 103 into a digital signal and supplying the digital signal to the interface 102; a central processing unit (CPU) 105 designed to control the operation of the interface device 102 and store data on the analysis of a specimen; and a printer 106 for printing out required information upon receipt of data on the analysis of the specimen.

A signal instructing the drive of a specimen-feeding pump is supplied from the control circuit 100 to the specimen-feeding pump assembly 31. Signals are issued from the control circuit 100 to the first and second reagent-feeding pumps 43, 44 for their drive through the corresponding signal lines 108, 109. Signals are sent forth from the control circuit 100 to the solenoid mechanism 76 through the signal lines 110, 111, 112 to drive the nozzles 40, 57, 58. A signal is supplied from the control circuit 100 to the specimen cassette 25 through the signal line 113 for the drive of said specimen cassette 25. A reagent cassette-driving signal is delivered from the control circuit 100 to the reagent cassette 26 and its drive motor 28 through the signal line 114. A signal is also issued from the control circuit 100 to the pulse motor 73 for its drive through the signal line 115 in order to effect the movement of the carrier member 67. Data on a specimen to be examined is delivered from the interface device 102 to the specimen cassette 25 through the signal line 116.

Upon receipt of output signals from the control circuit 100 and interface device 102, the specimen cassette 25 is also laterally moved (though not shown in FIG. 2) to cause specimens to be successively brought to a point at which they are sucked into the nozzles. A plurality of specimens are laterally arranged in the specimen cassette 25.

Description is now given of the operation of an automated chemical analytic apparatus embodying this invention. The direction of the arrow A of FIG. 2 in which the reaction line 14 travels denotes that in which a reaction time passes (hereinafter referred to as "a time axis direction"). A container 21 holding a plurality of specimens is placed in the specimen cassette 25. The first and second reagent containers 22, 23 are received in the reagent cassette 26. At this time, the carrier member 67 is set at a starting position S facing the second waste receptacle 24 acting as a drain.

The examiner operates a keyboard mounted on the operation panel 101. Upon receipt of a signal from the keyboard, the required one of the specimen containers held in the specimen cassette 25 and the required ones of the first and second reagent containers held in the reagent cassette 26 are brought to a point at which the specimen and reagent are to be sucked up into the corresponding nozzles. At this time, the control circuit 100 sends forth signals denoting data on a specimen to be examined, items of examination and a length of time in which analysis should be finished.

Thereafter, the following procedures are automatically carried out in accordance with a preset program. First, demineralized water is filled in the nozzles 40, 57, 58 disposed above the carrier member 67 waiting for actuation at the starting position S. Referring to the specimen-feeding pump assembly 31, the pulse motor 34 is driven upon receipt of a drive signal. The syringe starts sucking by means of the lead screw 35 and nut member 36. The electromagnetic valve 37 is actuated to take in demineralized water. Where the electromagnetic valve 37 is actuated in the opposite direction to cause the syringe 38 to carry out further suction, then demineralized water W is filled in the nozzle 40 and an air bubble P is formed at the lower end 40a of the nozzle 40 as shown in enlargement in FIG. 7. The air bubble acts to separate the demineralized water from a specimen or reagent. The above-mentioned arrangement is also applied to the other nozzles 57, 58.

During the above-mentioned procedure steps, the pulse motor 73 is driven to move the carrier member 67 in a direction opposite to that in which the reaction proceeds, thereby causing the specimen nozzle 40 to be brought to rest at a point facing the specimen container 21. The solenoid 77 is deenergized to let the nozzle 40 fall as shown in FIG. 2. The specimen-feeding pump assembly 31 is actuated to suck up a prescribed amount of a specimen. Later, the solenoid 77 is again energized to lift the specimen nozzle 40.

Figure 3:
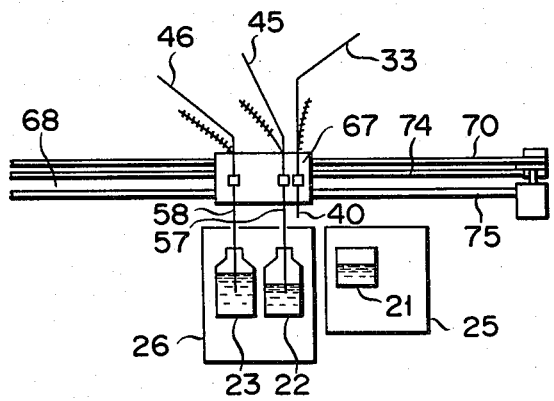
FIGS. 3 and 4 are fractional views of the analytic apparatus of the invention shown in FIG. 2.

Thereafter, the carrier member 67 is slightly moved in the direction in which reaction proceeds, causing both nozzles 57, 58 to exactly face the first and second reagent containers 22, 23. Later where the solenoid 77 is deenergized, both nozzles 57, 58 are brought down to suck up the first and second reagents as shown in FIG. 3. After suction is brought to an end, both nozzles 57, 58 are lifted. Since a distance $l_2$ between both nozzles 57, 58 is made equal to that between the centers of the first and second reagent containers 22, 23, the simultaneous suction of the first and second reagents can be effected, thereby reducing a time to suck up a specimen liquid and reagent (hereinafter simply referred to as a "suction time").

Figure 4:
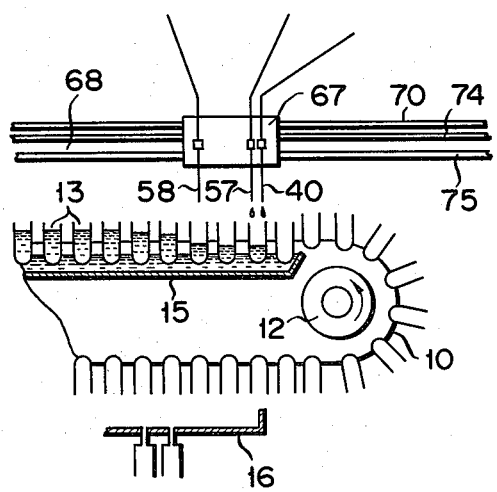

The carrier member 67 travels through the path 68 in the time axis direction, and is brought to rest at a point facing the selected one of the reaction tubes 13 as shown in FIG. 4. A specimen liquid is drawn into the selected reaction tube 13 through the specimen nozzle 40. The first reagent is simultaneously pipetted into the reaction tube 13 through the first reagent nozzle 57. This simultaneous introduction into the reaction tube 13 of both nozzles 40, 57 can be effected, because a distance $l_1$ between said nozzles 40, 57 is made shorter than the diameter of the opening of the reaction tube 13. Therefore the suction time can be shorted as previously described.

The second reagent is pipetted into the selected reaction tube through the second reagent nozzle 58, when the carrier member 67 is further moved in the time axis direction and brought near the terminal end of the reaction line (FIG. 2). This arrangement is specified for the case where the second reagent quickly reacts.

Where the pipetting of the specimen liquid and first and second reagents is brought to an end, then the carrier member 67 is brought back to the original position S by the backward drive of the pulse motor 73. At this time, the specimen nozzle 40 and first reagent nozzle 57 are brought down into the waste receptacle 24 to cause liquids left in both nozzles 40, 57 to be discharged. Thereafter, the carrier member 67 is slightly moved to the right as viewed in FIG. 2 to cause the second reagent nozzle 58 to face the waste receptacle, thereby releasing the reagent left in the second reagent nozzle 58. The release of the residual specimen liquid and first and second reagents left in the corresponding nozzles is effected by the forceful introduction of deionized water into said nozzles. Therefore, the inner walls of the nozzles are automatically washed by deionized water.

If arrangement is made to let deionized water be always ejected from another waste receptacle, then the outer walls of the nozzles can be washed by the deionized water when the residual liquids are discharged from the nozzles. It may be advised, however, to provide a separate washing device aside the waste receptacle 24.

Where the carrier member 67 is quickly brought to a required point on the reaction line 14 by the selective drive of the pulse motor 73, then a specimen liquid and reagents can be easily pipetted into a desired reaction tube 13, thereby making it possible to freely chose a reaction time.

The specimen liquid and reagents are carried along the reaction line 14 in a state sucked into the corresponding nozzles alone. Therefore, the exchange of a specimen liquid and reagents can be easily conducted simply by discharging extremely small residues of used specimen liquid and reagents, thereby assuring the saving of a specimen liquid and reagents to be applied.

Control of a timing in which a specimen liquid and reagents are pipetted from the corresponding nozzles as well as of a distance through which a carrier member is to be moved can be easily undertaken by those skilled in the art by providing a proper program for each of the control circuits.

Description is now given with reference to FIGS. 8 and 9 of a discrete type automated chemical analytic apparatus according to another embodiment of this invention. The parts of FIGS. 8 and 9 the same as those of the first embodiment are denoted by the same reference numerals, description thereof being omitted. The second embodiment is different from the first embodiment in that the common carrier member 67 of the first embodiment is replaced by a carrier member 67a for the specimen nozzle 40, a carrier member 67b for the first reagent nozzle 57 and a carrier member 67c for the second reagent nozzle 58, in other words, the respective nozzles 40, 57, 58 are mounted on the corresponding carrier members 67a, 67b, 67c to be driven separately.

The three carrier members 67a, 67b, 67c of the second embodiment are provided, as seen from FIG. 9, with separately driven timing belts 70a, 70b, 70c, upper guide bars 74a, 74b, 74c and lower guide bars 75a, 75b, 75c. The three carrier members 67a, 67b, 67c are spatially arranged in parallel with the reaction line 14. The timing belts 70a, 70b, 70c corresponding to the carrier members 67a, 67b, 67c are driven by the individual drive motors 73a, 73b, 73c (FIG. 8) by means of the corresponding pulleys. These drive motors 73a, 73b, 73c are connected to the control circuit 100 through lines 115a, 115b, 115c branched from a main line 115.

Individual control of the three drive pulse motors 73a, 73b, 73c of the second embodiment for the independent movement of the three carrier members 67a, 67b, 67c can be easily effected by those skilled in the art by providing a proper program for each of the control circuits.

What is important for the present invention is that the specimen nozzle and reagent nozzles can be moved to any desired point on a reaction line, thereby enabling the specimen liquid, and reagents to be pipetted into any selected reaction tube. Therefore, the collective or individual movement of the specimen nozzle and reagent nozzles is simply a matter of design. It will be noted that nozzle-driving solenoid mechanisms are omitted from FIG. 8 for the sake of the description.

With the first and second embodiments, reference has been made to the case where two reagents were applied. However, the number of reagents need not be limited to two. It is possible to use a single reagent or simultaneously pipette three or more reagents.

With the second embodiment, the carrier members 67a, 67b, 67c are spatially arranged, as shown in FIG. 9, laterally of the analytic apparatus. Therefore, the lower portions of the specimen nozzle 40, first reagent nozzle 57 and the second reagent nozzle 58 are bent convergently to approach each other as much as possible, so that the tips of the nozzles 40, 57, 58 are aligned along the reaction line 14.

With the second embodiment, description has been given of the so-called single channel type analytic apparatus. However, a multichannel type analytic apparatus can be provided by arranging two reaction lines constructed in the same manner as in the single type laterally in parallel with each other.

What is claimed is:

1. A discrete type automated chemical analytic apparatus for continuously analyzing a large number of specimens with respect to a plurality of items of examination in a single reaction channel comprising:
    endless belt conveyor means having a top run;
    drive means for moving the endless belt conveyor means;
    a plurality of reaction tubes spatially arranged in the direction in which the conveyor means is moved, those of the reaction tubes which are positioned on the top run of the conveyor means defining a reaction line, the direction in which the reaction line travels being a time axis direction;
    specimen holding means;
    reagent holding means;
    specimen discharge means for delivering a specimen from said specimen holding means to a selected reaction tube mounted on the reaction line, said specimen discharge means including conduit means;
    reagent discharge means for delivering one or more reagents to said selected reaction tube on the reaction line, said reagent discharge means including conduit means;
    measuring means provided at the terminal end of the reaction line for analyzing said reacted specimen at a fixed measuring point on the reaction line;
    means for washing and drying the reaction tubes after removal of said specimen in order to render them ready for the subsequent application;
    carrier means for moving the conduit means of the specimen discharge means and the conduit means of the reagent discharge means from a point facing the specimen holding means and the reagent holding means to selected points along the time axis direction facing the selected one of the reaction tubes mounted on the reaction line, said carrier means being constructed and selectively movable to deliver the specimen and the reagent to the selected reaction tube at the same point and at a different point on the reaction line in the time axis direction;
    means for driving said carrier means;
    whereby a reaction time can be properly controlled in accordance with a kind of specimen and items of examination.

2. The automated analytic apparatus according to claim 1, wherein the carrier means is formed of a single carrier member for supporting the conduit means of the specimen discharge means and the conduit means of the reagent discharge means.

3. The automated analytic apparatus according to claim 1, wherein the carrier means includes a carrier member for supporting the conduit means of the specimen discharge means and other carrier members for supporting the conduit means of the reagent discharge means.

4. The automated analytic apparatus according to claim 1, wherein the specimen-holding means and reagent-holding means are linearly arranged side by side over the extension of the starting portion of the reaction line of the conveyor means.

5. The automated analytic apparatus according to claim 1, which further comprises guide means connected to the carrier means to guide the movement of the carrier means through the path.

6. The automated analytic apparatus according to claim 1, wherein the drive means includes:
    timing belt means fixed to the carrier means and extended along the path of the carrier means;
    a pair of pulley means across which the belt means is stretched; and
    drive motor means connected to one of said pulley means.

7. The automated analytic apparatus according to claim 2, wherein the conduit means of the specimen discharge means includes a first nozzle open at the bottom; the conduit means of the reagent discharge means includes at least another nozzle open at the bottom; and said first and another nozzles are spatially mounted on the single carrier means in a vertically movable state.

8. The automated analytic apparatus according to claim 2, wherein the conduit means of the specimen discharge means includes a first nozzle open at the lower end; the conduit means of the reagent discharge means comprises nozzles open at the lower end; the nozzles are spatially arranged in a vertically movable state; the reagent-holding means is formed of two reagent containers corresponding to the second and third nozzles of the reagent discharge means.

9. The automated analytic apparatus according to claim 8, wherein a distance between the first nozzle and the center of either of the second and third nozzles is made smaller than the diameter of the opening of the respective reaction tubes.

10. The automated analytic apparatus according to claim 9, wherein a distance between the second and third nozzles is made equal to a distance between the centers of the two reagent containers.

11. The automated analytic apparatus according to claim 4, which further comprises another waste-receiving means disposed above the extension of the reaction line aside the specimen-holding means and reagent-holding means to recover a waste residual solution from the conduit means of the specimen discharge means and those of the reagent discharge means.

12. The automated analytic apparatus according to claim 1, wherein the conduit means of the specimen discharge means includes a first vertically extending nozzle open at the lower end; the conduit means of the reagent discharge means includes second and third vertically extending nozzles open at the lower end; the carrier means includes a vertically extending wall plate, three vertical slots spatially formed in said vertically extending wall plate, support elements which are made vertically slidable through said slots and are penetrated by the first, second and third nozzles, an upper block laterally projecting from one side of the upper portion of the vertically extending wall plate, and a lower block laterally projecting from one side of the lower portion of said vertically extending wall plate; and the drive means includes: timing belts extending through the path and fixed to the upper block of the carrier means, a pair of pulleys across which said belts are stretched, and drive motors connected to either of said pulleys.

13. The automated analytic apparatus according to claim 12, which further comprises guide means for guiding the movement of the carrier means through the path, said guide means being formed of a first elongated guide bar slidably engaged with the upper block of the carrier means, rollers rotatably fitted to a lower block of the carrier means and a second elongated guide bar extending along the path and slidably engageable with the rollers.

14. The automated analytic apparatus according to claim 1, wherein the carrier means are formed of first, second and third carrier members, the first carrier member supporting the conduit means of the specimen discharge means, and the second and third carrier members supporting the two conduit means of the reagent discharge means; the drive means includes first, second and third elongated belts spatially extending through the path substantially in paralel with each other, pulley means across which said belts are stretched, and drive motors disposed to face the respective belts for their individual drive; and the first, second and third carrier members are respectively fixed to the first, second and third belts to be selectively moved through the path.

15. The automated analytic apparatus according to claim 12, wherein the upper and lower blocks are bridged by guide rods for guiding the vertical movement of the support elements; a compression spring surrounds that portion of each guide rod which is defined between the underside of the upper block and the surface of each support element; the respective support elements are electromagnetically actuated toward the upper block against the urging force of the corresponding compression springs, thereby normally holding the nozzles in the lifted position.

* * * * *